(12) United States Patent
Doorly et al.

(10) Patent No.: US 6,554,856 B1
(45) Date of Patent: Apr. 29, 2003

(54) STENTS FOR BLOOD VESSELS

(75) Inventors: Denis Joseph Doorly, London (GB); Colin Gerald Caro, London (GB); Mary Anne McLean, Rickmansworth (GB)

(73) Assignee: Imperial College of Science, Technology & Medicine, London (GB)

( * ) Notice: Subject to any disclaimer, the term of this patent is extended or adjusted under 35 U.S.C. 154(b) by 0 days.

(21) Appl. No.: 09/424,695
(22) PCT Filed: May 27, 1998
(86) PCT No.: PCT/GB98/01529
§ 371 (c)(1), (2), (4) Date: Feb. 22, 2000
(87) PCT Pub. No.: WO98/53764
PCT Pub. Date: Dec. 3, 1998

(30) Foreign Application Priority Data

May 27, 1997 (GB) ............................................ 9710905

(51) Int. Cl.[7] .................................................. A61F 2/06
(52) U.S. Cl. ..................................................... 623/1.15
(58) Field of Search ................................ 623/1.1, 1.11, 623/1.12, 1.13, 1.14, 1.15, 1.16, 1.17, 1.18, 1.19, 1.2, 1.21, 1.22; 606/108, 191, 194, 195, 198, 153, 151

(56) References Cited

U.S. PATENT DOCUMENTS

| 5,156,619 A | * | 10/1992 | Ehrenfeld ........................ 623/1 |
| 5,968,089 A | * | 10/1999 | Krajicek ......................... 623/1 |
| 6,039,754 A | * | 3/2000 | Caro .............................. 623/1 |
| 6,241,741 B1 | * | 6/2001 | Duhaylongsod et al. ..... 606/153 |

* cited by examiner

Primary Examiner—Kevin T. Truong
Assistant Examiner—Vy Q. Bui
(74) Attorney, Agent, or Firm—Fay, Sharpe, Fagan, Minnich & McKee, LLP

(57) ABSTRACT

A stent for supporting part of a blood vessel which stent includes a supporting portion around which or within which part of a blood vessel intended for grafting can be placed so that the stent internally or externally supports that part and the supporting portion of the stent is of a shape and/or orientation whereby flow between graft and host vessel is caused to follow a non-planar curve. By maintaining non-planar curvature in the graft itself, favorable blood flow velocity patterns can be achieved through generation therein of 'swirl' flow. Failures in such grafts through blockage, kinking or collapse, can be significantly reduced.

9 Claims, 4 Drawing Sheets

STENTS FOR BLOOD VESSELS

Figure 1A:
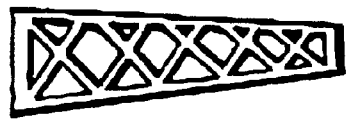

This invention is concerned with stents for supporting parts of blood vessels. More particularly it is concerned with stents such as supporting devices for arterial or venous grafts.

Stents are known devices used in surgery especially in vascular surgery for providing physical support to a blood vessel i.e. they can be used to help prevent kinking and/or collapse of blood vessels such as veins or arteries.

It has been proposed that vascular prostheses may incorporate non-planar curvature to improve blood flow velocity patterns by skewing the motion to induce 'swirl' flow to the blood circulating through the prosthesis.

We have now devised an apparatus and technique for establishing and/or maintaining non-planar curvature within arterial and/or venous grafts e.g. in blood vessel bypass surgery wherein the graft is a donor part from another blood vessel from the patient, which part is to be surgically connected to create a bypass in a blocked, constricted or otherwise blood flow-restricted vessel.

By maintaining non-planar curvature in the graft itself, favourable blood flow velocity patterns can be achieved through generation therein of 'swirl' flow. Failures in such grafts through blockage, kinking or collapse, can be significantly reduced.

According to this invention there is provided a stent for supporting part of a blood vessel which stent includes a supporting portion around which or within which part of a blood vessel intended for grafting can be placed so that the stent internally or externally supports that part and the supporting portion of the stent is of a shape and/or orientation whereby flow between graft and host vessel is caused to follow a non-planar curve.

The supporting portion of the stent may be fabricated to incorporate:

(i) a non-planar curved form and/or
(ii) a geometric arrangement of the junction between graft and host vessel e.g. artery whereby the tangent vector from the centreline of the graft does not intersect the centreline of the host vessel by consequence of an asymmetric disposition of the graft with respect to that host vessel at the junction with the graft.

The stent may be of generally hollow tubular shape with three dimensional curvature. The stent is particularly preferred for use in supporting such blood vessel parts as arterial and venous grafts, such as the living donor vessels. used in bypass surgery.

The stent may take the form of an open lattice generally tubular framework with discrete openings at each end thereof.

A blood vessel part such as an arterial graft may be passed through the interior section of e.g. a partially coiled tubular stent, which stent then provides support for that part of the graft which passes through its interior, and which thereby imparts to that graft a geometry which includes non-planar curvature i.e. the vessel part supported by the stent can assume and maintain curvature which is non-linear. Part of the supported vessel in such embodiments thereby acquires a geometry which can be regarded as a part-helical curve even if the physical extent of the supported vessel is less than one complete turn of a helix e.g. less than ½ or less than ¼ of such a turn.

In other embodiments of the invention, the stent can comprise a first supporting structure adapted to support or otherwise contact part of the vessel to be bypassed, with a secondary supporting structure attached to and extending away from the first supporting structure, but simultaneously supporting the arterial or venous graft. The secondary such supporting structure may, for example, comprise a plurality of elongate members linked or connected in the region of their ends remote from the first supporting structure.

Such elongate members can be fabricated such that between them they define a curved section wherein the curvature is non-planar. Such an arrangement is particularly suited to an external stent for supporting the graft vessel at either or both physical junctions of the graft, as in a typical venous or arterial graft sites.

A practical embodiment of a non-planar internal stent is one fabricated from a shape memory alloy, formed to adept an appropriately helical or part-helical form, to provide the required support for the graft after insertion.

Figure 1B:
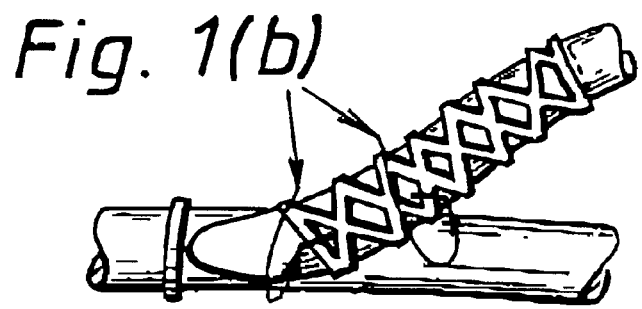
Figure 1C:
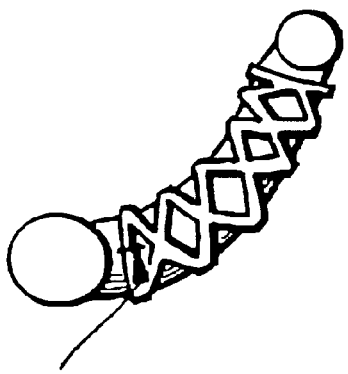
Figure 2:
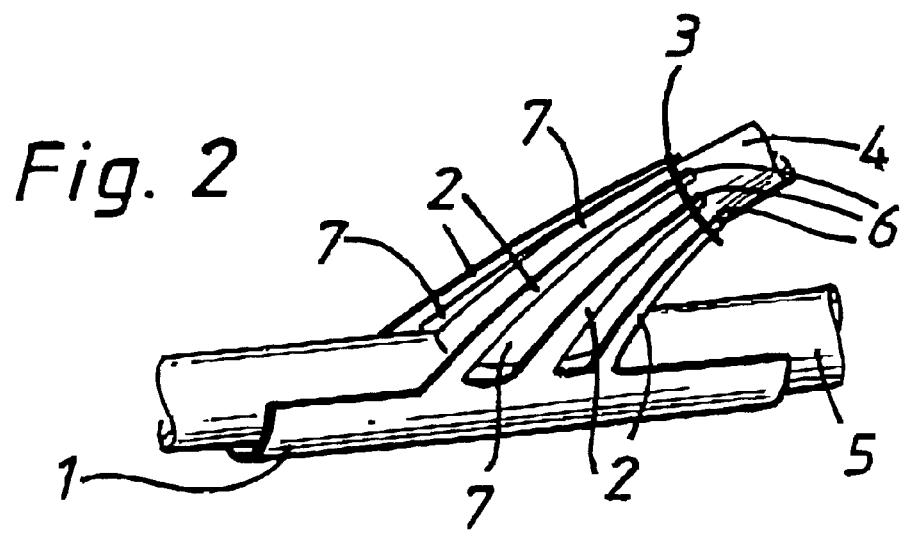
Figure 3:
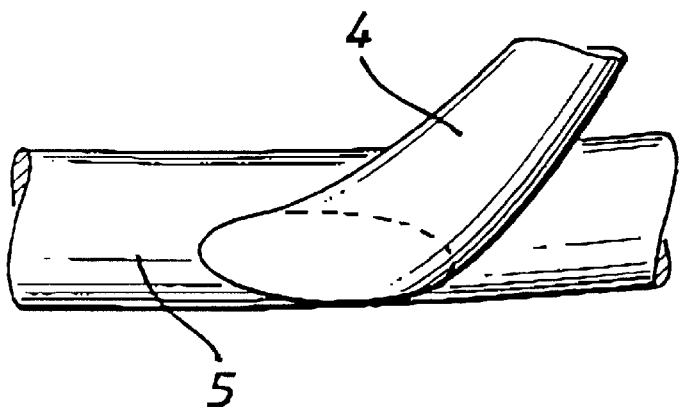
Figure 3A:
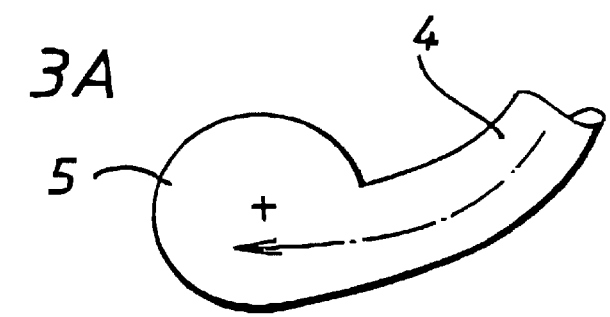
Figure 4:
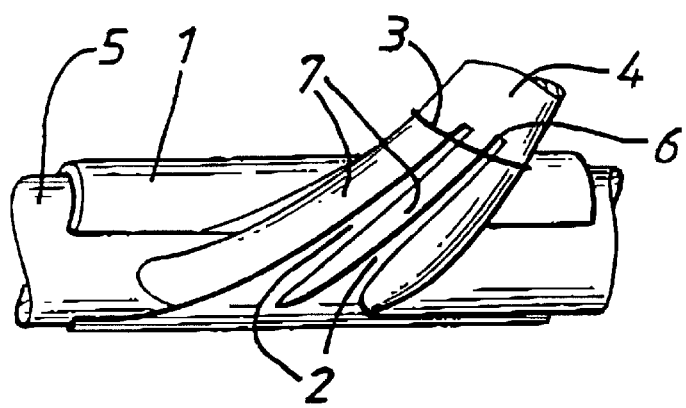
Figure 4A:
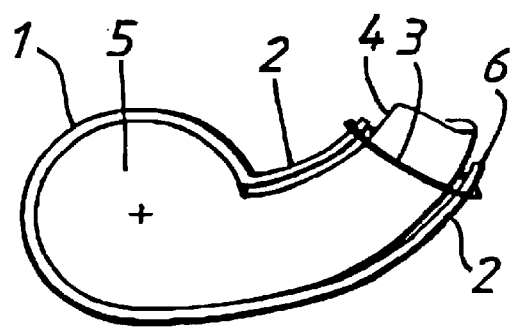
Figure 5:
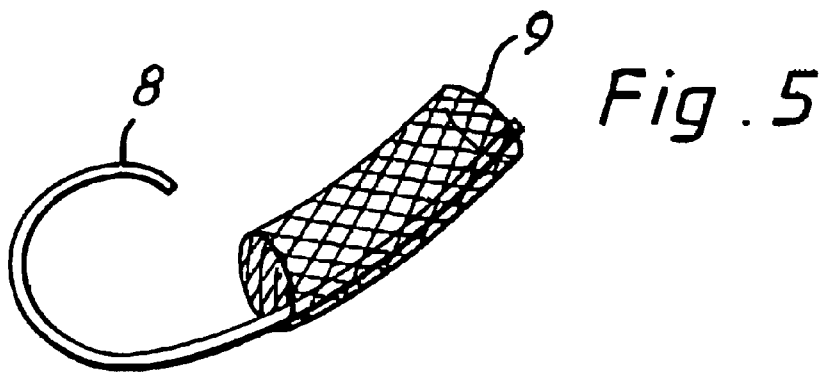
Figure 6A:
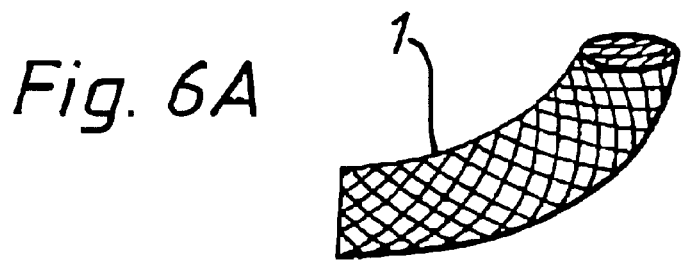
Figure 6B:
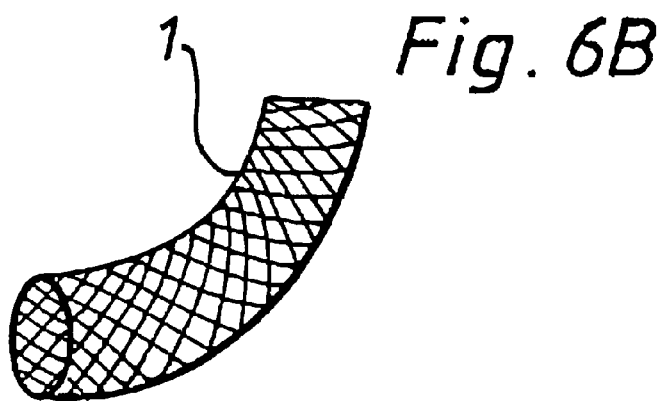
Figure 6C:
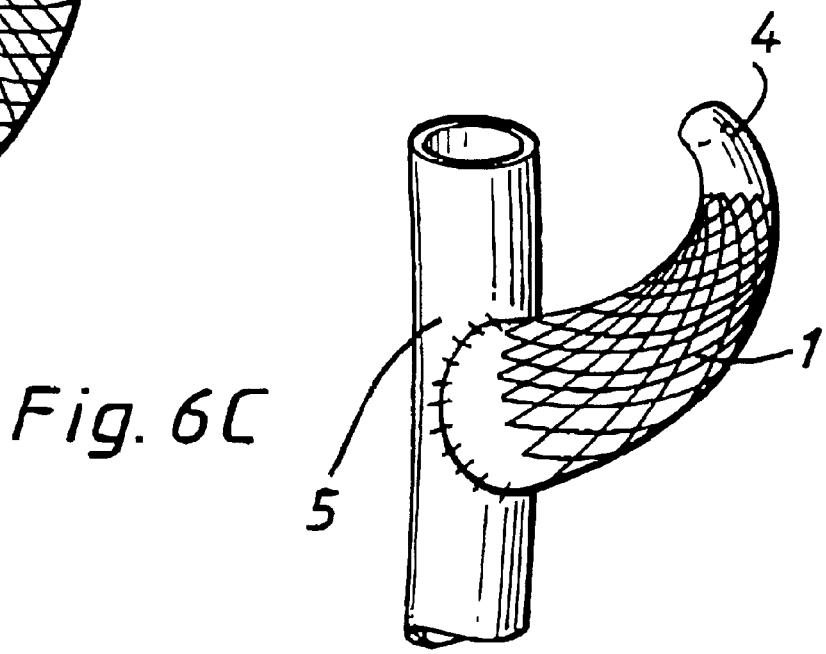
Figure 7A:
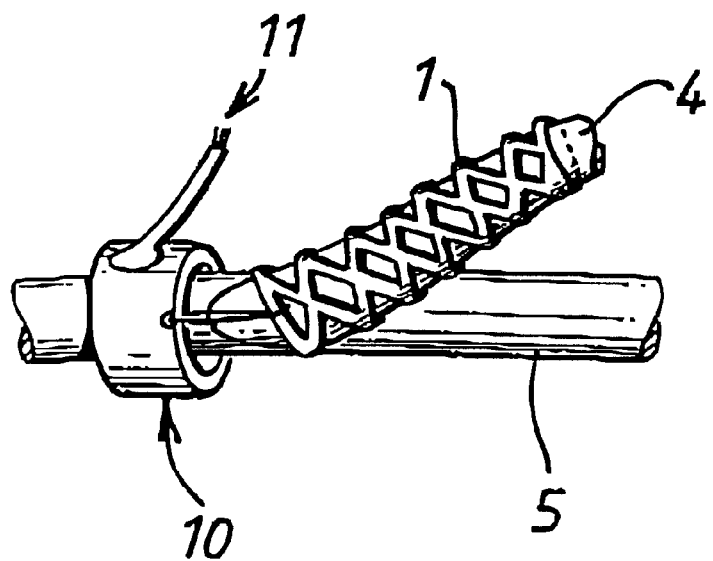
Figure 7B:
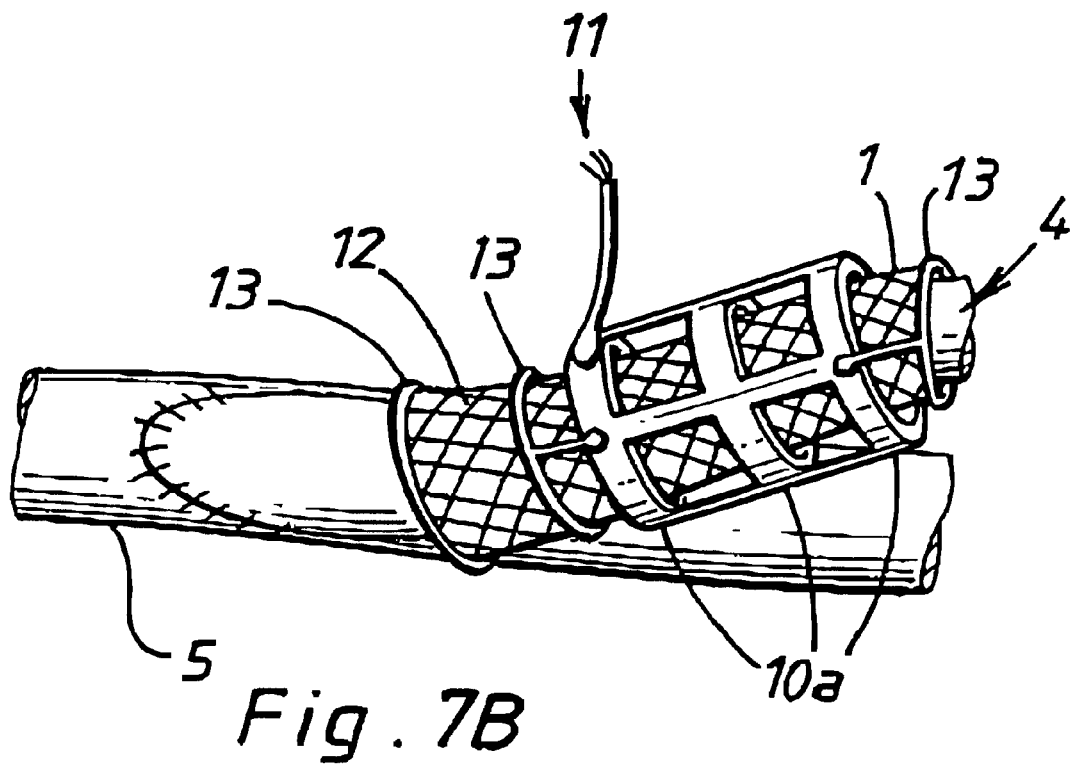

In order that the invention may be illustrated, more easily understood and readily carried into effect by one skilled in this art, reference will now be made to the accompanying drawings of preferred embodiments by way of non-limiting example only, and in which:

FIGS. 1*a* to *c* depict an embodiment of an external stint shaped to conform the graft part in non-planar curvature at a site of arterial graft, FIG. 2 shows an alternative embodiment of an external stent, FIG. 3 shows a configuration of artery with a graft vessel attached tangentially to the arterial wall, FIG. 3*a* is a side view of the FIG. 3 arrangement, FIG. 4 shows one suitably shaped external stent adapted to establish and maintain non-planar curvature in an arterial graft part as shown in FIGS. 3 and 3*a*, FIG. 4*a* is a side view of the FIG. 4 supported graft site, FIG. 5 is an alternative embodiment of an internal stent based on a clip of e.g. shape memory alloy, FIGS. 6*a* and 6*b* show a part-helical internal FIG. 6*c* shows the stent of FIGS. 6*a* /6*b* internally supporting an arterial graft part, FIG. 7*a* shows a bypassed artery, an externally, located stent for the graft and a sensor for transmitting flow data, and FIG. 7*b* shows a similar arrangement to FIG. 7*a* but wherein the sensor is located around the supported graft part.

Referring to FIGS. 1*a* to *c* of the drawings, the device shown may be fabricated from a thermosettable plastic, in the form of a hollow tube, the walls of which contain numerous openings so that the exterior of the graft is not fully shielded.

In particular, FIG. 1(*a*) shows the stent before thermosetting, whereas FIGS. 1(*b*) and (*c*) indicate possible configurations whereby prior thernosetting has rendered this stent to adopt the shape of a partially coiled, non-planar curve.

The stent is then inserted over the graft to ensure the geometrical configuration of graft and host vessels, e.g. arteries adopt a predetermined form in the locality of the graft.

The stent may be of constant diameter, or tapered, as in FIG. 1(*a*) to accommodate the common practice of enlarging the graft in the vicinity of its junction with the host artery. The stent may be fixed to the graft by sutures (shown arrowed) or to avoid trauma to the graft, may be attached to a clip ring placed about the host vessel.

The restraining action of the stent may be graduated, by mechanically "tapering" the rigidity of the material: for example, at either end, material may be removed or the rigidity reduced by cuttings. An internally locatable stent is also provided which corresponds to the external stent just described, however such a stent is inserted into the interior of the graft vessel part rather than being placed exterior to the graft.

Referring to FIG. 2 the non-planarity of the graft 4 is attained by supporting it with an external stent 1, 2 which comprises a longitudinal part section 1 of a cylinder, fabricated of a suitable porous biocompatible material, which may be of straight or curved section, to support that part of the artery 5 in the region of the graft, and integral with part section 1, or attached securely thereto are a plurality of elongate external support members 2, which are fabricated to define an internal region 7 of appropriate non-planar geometry.

The ends 6 of the support members 2 may be secured in situ by surgical thread (not shown) or by a fastening ring 3. The grafted vessel 4 is located within that internal region 7.

FIGS. 3 and 3a depict a non-planar configuration of graft and artery wherein an arterial graft (artery 5, graft 4) having a non-planar curve is surgically attached offset to the central portion of the artery 5 in that it is at least partly tangential to the artery, see the direction of flow arrow in FIG. 3a.

The external stent (1,2) of FIG. 2 can be modified to support and maintain the non-planar curvature of the graft in the FIGS. 3/3a arrangements, by for example the structure as depicted in FIGS. 4/4a. FIGS. 4 and 4a have reference numerals which correspond with those used in FIG. 2 described above.

As shown in FIG. 5 an internal stent for establishing and/or maintaining nonplanar curvature of a graft (vessel part) comprises a clip 8 which is part coiled or at least part helical of shape memory alloy, affixed to a cylindrical wire mesh 9.

FIGS. 6A and 6B show an alternative embodiment of an internal stent, in which the stent 1 is fabricated from a linked wire mesh of part helical form. The material used is preferably a shape memory alloy to facilitate insertion of the stent. FIG. 6C shows the stent located in the graft post insertion. The graft 4 surgically attached to artery 5 has been shown 'transparent' for purposes of illustration, to show the internally located, part helical wire mesh stent in-situ.

Referring to FIGS. 7A and 7B, either internal or external stents may incorporate devices which assist in monitoring the condition of either the graft or the host vessel or both.

In one possible embodiment shown in FIG. 7A, an external stent 1 incorporates a sensor portion 10 for monitoring the condition of the host artery. The sensor portion is a ring placed over the host artery 5, attached to the tubular stent 1 placed over the graft. The sensor and stent may be secured together by means of clips or threads during the operation to insert the graft. The sensor 10 may incorporate one or several ultrasound probes, or it may comprise a coil for use with magnetic resonance imaging. The sensor portion may be electrically connected by leads 11, only partly shown, to a remote module or modules (nor shown) which incorporate the required power supply, signal detection and recording devices for data capture and transmission. Some or all of the modules to which the sensor is connected may be implanted within the body of the person receiving the graft, and incorporate appropriate means such as telemetry for transcutaneous data monitoring.

In a still further embodiment shown in FIG. 7B, an external stent 1 comprises a fabric or porous structure 12 attached to several outer supporting members, having the external appearance of linked rings or discs 13. For a portion of the stent, these outer members incorporate a sensor device 10a or series of sensors such as miniature radiofrequency and/or gradient coils for magnetic resonance imaging, or ultrasound transducers. The power supply for the sensors, excitation and data monitoring may be as in the FIG. 7A embodiment. Electrical wires 11 connect the sensor device 10a to the appropriate remote module or modules (not shown).

In other embodiments of an internal or external stent, the sensory action of the stent may derive from the construction of some or all of the supporting members which form the stent. In one such embodiment, the sensory action derives from a coil or coils of an electrically conducting material wound around the perimeter of the stent or interspersed at intervals along the stent which coil or coils may be excited by extracorporeal magnetic and/or electromagnetic fields, and the signal from the stent detected by magnetic coupling with an external detecting coil.

What is claimed is:

1. A stent for supporting part of a graft which stent includes a supporting portion around which or within which an associated graft can be placed so that the stent internally or externally supports the associated graft and the supporting portion of the stent is fabricated to incorporate a non-planar curved form whereby flow between the associated graft and an associated host vessel is caused to follow a non-planar curve and including a further supporting portion, around which or within which the associated host vessel can be placed, for locating the associated graft wherein said supporting portion is fabricated to impose a geometric arrangement at a junction between said supporting portion and said further supporting portion whereby a tangent vector projected from a centerline of the associated graft, at said junction, does not intersect a centerline of the associated vessel by consequence of an asymmetric disposition of the further supporting portion with respect to the supporting portion at said junction.

2. A stent as claimed in claim 1 which is of generally hollow tubular shape with three-dimensional curvature.

3. A stent as claimed in claim 1 fabricated from a shape memory alloy.

4. A stent for supporting part of a graft which stent includes a supporting portion around which or within which an associated graft can be placed so that the stent internally or externally supports the associated graft and the supporting portion of the stent is fabricated to incorporate a non-planar curved form whereby flow between the associated graft and an associated host vessel is caused to follow a non-planar curve and further comprising a first supporting structure adapted to support or otherwise contact part of the vessel to be bypassed, and a secondary supporting structure extending angularly away from the first supporting structure, but simultaneously capable of supporting the graft vessel part, said secondary structure capable of maintaining a graft vessel part when located therein in non-planar curvature.

5. A stent as claimed in claim 4 wherein the secondary supporting structure comprises a plurality of elongate members linked in the region of their ends remote from the first supporting structure.

6. A stent as claimed in claim 4 wherein said elongate members define a curved section whose curvature is non-planar.

7. A stent for supporting part of a graft which stent includes a supporting portion around which or within which an associated graft can be placed so that the stent internally or externally supports the associated graft and the supporting portion of the stent is fabricated to incorporate a non-planar curved form whereby flow between the associated graft and an associated host vessel is caused to follow a non-planar curve and comprising a further supporting portion (1) adapted to support or otherwise contact part of a vessel to be bypassed, with the supporting portion extending annularly away from the further supporting portion (1).

8. A stent as claimed in claim 7 wherein the supporting portion comprises a plurality of elongate members (2) linked in the region of their ends remote from the further supporting portion.

9. A stent as claimed in claim 7 wherein the further supporting portion (1) and the supporting portion have a geometric arrangement at a junction between them whereby the tangent vector from the centreline of the supporting portion does not intersect the centreline of the further supportion portion (1) by consequence of an asymmetric disposition of the supporting portion with respect to the further supportion portion (1).

* * * * *